United States Patent [19]

Young et al.

[11] Patent Number: 5,033,461
[45] Date of Patent: Jul. 23, 1991

[54] ORTHOPAEDIC BRACE

[75] Inventors: David E. Young, Watlington; Kenneth P. Davis, Hillington, both of England

[73] Assignee: Protectair Limited, Abingdon, England

[21] Appl. No.: 404,193

[22] Filed: Sep. 7, 1989

[30] Foreign Application Priority Data

Sep. 12, 1988 [GB] United Kingdom ............... 8821360

[51] Int. Cl.⁵ .............................................. A61F 5/00
[52] U.S. Cl. .................................................... 128/88
[58] Field of Search ............... 128/25 R, 88, 94, 77, 128/99.1, 83, 78, 80 A

[56] References Cited

U.S. PATENT DOCUMENTS

| 1,257,297 | 2/1918 | Brown. | |
|---|---|---|---|
| 1,768,770 | 7/1930 | Kettelkamp. | |
| 2,191,283 | 2/1940 | Longfellow | 128/88 |
| 2,661,000 | 12/1953 | Gazeley et al. | 128/88 |
| 3,528,413 | 9/1970 | Aydt | 128/88 |
| 4,180,870 | 1/1980 | Radulovic et al. | 128/77 |
| 4,237,873 | 12/1980 | Terry et al. | 128/77 |
| 4,299,210 | 11/1981 | Santy | 128/88 |
| 4,373,517 | 2/1983 | Criscuolo | 128/75 |
| 4,417,569 | 11/1983 | Brudny | 128/77 |
| 4,497,316 | 2/1985 | Lilla | 128/94 |
| 4,559,932 | 12/1985 | Salort | 128/77 |
| 4,612,919 | 9/1986 | Best | 128/77 |
| 4,651,719 | 3/1987 | Funk et al. | 128/25 R |
| 4,669,451 | 6/1987 | Blauth et al. | 128/25 R |
| 4,896,660 | 1/1990 | Scott | 128/94 |

Primary Examiner—Richard J. Apley
Assistant Examiner—Glenn E. Richman
Attorney, Agent, or Firm—Tilton, Fallon, Lungmus

[57] ABSTRACT

An orthopaedic brace for the upper limb comprising a mounting member adapted to be fastened to the torso of a patient, an arm support pivotally mounted on the mounting member for movement about vertical and horizontal axes, and an adjustment mechanism for raising and lowering the arm support about the horizontal axis to enable the shoulder joint of the patient to be abducted over a continuous range from a low abduction angle to a high adduction angle and adducted over a continuous range from a high abduction angle to a low abduction angle.

10 Claims, 5 Drawing Sheets

ORTHOPAEDIC BRACE

BACKGROUND AND SUMMARY

This invention relates to orthopaedic braces and particularly to an orthopaedic shoulder brace which is readily adjustable to provide a wide range of fixed and movable orientations.

Bracing of the upper limb has been a relatively neglected field. Probably the main reason for this is that the lower limbs are weight bearing and significant damage or deformity to the lower limbs restricts mobility. Bracing can often restore this, obviating the need for a wheelchair or crutches. Also, there is a wider variety of major orthopaedic surgical procedures carried out on the lower limb including total hip and total knee replacement. With the exception of the hand, there are fewer on the upper limb and consequently the drive to brace it has been less. Furthermore, the technique of arthroscopy —viewing (and operating upon) the interior of a joint via a hollow tube carrying a fibre optic viewing system—was applied much sooner to the knee than to the shoulder.

However, in the last few years shoulder arthroscopy has become very widely practised, especially in the U.S.A. Excision of glenoid labrum tears, surgery for recurrent posterior subluxation of the shoulder and decompression of the coracoacromial arch are now common procedures with high success rates carried out particularly in athletes who specialise in throwing such as baseball pitchers, football quarterbacks and javelin throwers.

After surgery, it is generally required to nurse the arm in an elevated position with the shoulder abducted to anything up to 90 degrees. Ideally, the shoulder will then be progressively taken out of abduction until held at only 45 degrees or 30 degrees. After this point is achieved, suspension of the arm will usually be abandoned.

Whilst the shoulder is abducted to the maximum desired position, it will normally be either locked in 0 degrees or 90 degrees (occasionally more) of flexion or allowed a range of motion such as 0 degrees-90 degrees or 0 degrees-135 degrees of flexion. In addition it is usually desired to control the elbow by locking it at 0 degrees, 90 degrees or 135 degrees of flexion or allowing a range of motion such as 0 degrees-90 degrees or 0 degrees-135 degrees. Support for the wrist also is desirable.

Most centres in the U.S.A. still rely on various types of sling made from bandages or stockinette. The device is usually prescribed in conjunction with intermittent exercises, generally supervised by a physical therapist, especially early in the post-operative period.

In 1986, the present inventors were shown part of a splint by a Greek doctor working in a British hospital. He claimed to have brought it from Toronto in Canada. This "Toronto" splint consisted of a plastics forearm gutter mounted on a flat aluminium bar connected to another flat aluminium bar carrying an upper arm gutter. The two flat bars formed a free unipivotal hinge but both had threaded holes which became aligned at 90 degrees elbow flexion. Presumably, in conjunction with a screw (which was not present), they formed a crude lock.

The shoulder hinge consisted of a first vertical member counterbored down its vertical axis from the top, and a second vertical member inserted into the first. The second member was able to rotate within the first member in a horizontal plane. A threaded hole in the side of the first vertical member communicated with the counterbore and a screw fitted into the hole provided a lock when driven in against the lower part of the second vertical member.

At the top of the second member there was provided a vertical discoid region with a radially toothed face and a horizontal central hole. A similar radially toothed discoid third member was secured to that described above by a central bolt and nut and was attached to the flat aluminium bar carrying the upper arm gutter. The enmeshed radial teeth enabled the arm elements to be suspended locked together over a wide range of positions. The remainder of the device (if indeed there were any other elements) was missing.

Recently the present inventors have encountered a splint produced by United States Manufacturing Company (USMC) of Pasadena, Calif., U.S.A. which is similar in most essentials to the so-called "Toronto Splint" described above. This has a first counterbored vertical member, a second inserted vertical member, a compression screw lock between the first and second vertical members, vertical first and second meshing radially toothed discoid regions secured by a nut and bolt and upper and lower arm gutters mounted on flat aluminium bars joined at the elbow to form a unipivotal hinge. The elbow hinge in this joint, however, has two locking positions at 90 degrees of flexion and 90 degrees of extension. Since extension of the elbow joint beyond 0 degrees or thereabouts is impossible, the purpose of the second position is presumably to make the device non-handed. The locking screws and holes are covered by a fleecy pad secured in position with tenacious adhesive; this does not make for easy adjustment or release.

The USMC device referred to above does have a rudimentary suspension system for attachment to the patient. It consists of a vertical metal bar attached to the first element of the shoulder hinge mechanism described above, a second vertical metal bar screwed to the first and having several extra holes, a plate attached to the first metal bar in the region corresponding to the patient's chest and a further plate attached to the second metal bar in the region of the patient's waist. The plates have straps for holding the device in place on the patient. All appropriate areas have fleecy pads.

Both the USMC brace and the "Toronto Splint" have similar serious limitations. Thus, the shoulder hinge is satisfactory in both cases in providing free flexion and extension, but the compression screw locking mechanism is easily overcome with moderate effort and is not satisfactorily secure; the USMC brace performed better under test than the "Toronto Splint".

Also, the control of abduction is discontinuous and in use the adjustment means is carried right up to the axilla—the most difficultly accessible location for it. Further, the elbow hinges of both devices offer only free or 90 degrees flexion positions and the locking screws are almost impossible to reach with the brace fitted on the patient.

However, the USMC device has no means of compensating the "lie" of the device on fat or shapely patients. For instance, when seen from the front on a fat patient, the device can take up a markedly angled position so that crude bending of the metal arms is necessary to get it to lie satisfactorily.

The present inventors have also seen in Italy a device for supporting the arm and shoulder called the Modello OK-740493 and supplied by W. Pabisch S.p.A., Milan, Italy. This comprises a lightweight harness and waistband carrying a vertical tubular strut which extends up to the shoulder and onto a shoulder (supra scapular) band. A second strut is directed posteriorly and is secured to the first strut by a compression screw mechanism. A third strut is attached to the second strut by a unipivotal hinge, attachment being in the form of a compression screw mechanism by means of which the device can be locked at any point. The third strut also carries an upper arm gutter and is attached at its distal end via another compression screw mechanism to a fourth strut, thus forming a unipivotal elbow hinge. The fourth strut carries a forearm gutter and terminates distally in a padded palm support.

There seem to be several features of this device which make it unsuitable for general use post arthroscopy of the shoulder. Thus, the presence of any shoulder pad is undesirable since it means that the perioperative site must be subjected to load which should be avoided; the second strut which is directed posteriorly is subjected to high torsional loads which could lead to fatigue of this component; the first strut runs very close to the operative site and could impinge upon or render difficult the changing of the dressing; the connection between first and second struts is limited by a compression screw which can readily slip; neither the shoulder hinge nor the elbow hinge offers range of motion control; and there does not appear to be any means by which the arm can be progressively taken out of abduction, although this may simply be misinterpretation of the photographs.

Physical Support Systems Inc. of Windham, N.H., U.S.A. offers a "Shoulder Subluxation Inhibitor" which is a shoulder orthosis designed to fulfil the function that its name implies. This device fits over and around the shoulder intimately and incorporates hyperextension and other stops. It does not offer progressive removal of the shoulder from a high abduction angle and there are no elbow and wrist components. It seems clear that this device is intended for a much later stage of shoulder rehabilitation than is the shoulder brace with which the invention is concerned. The intimate fit of the device would make it unsuitable for use in the early post-operative period following arthroscopy of the shoulder.

For the sake of completeness, reference is made also to U.S. Pat. No. 3,528,413 which describes an adjustable limb support used for instance to secure a limb to a stretcher rail. The main member is pivotally mounted on one end to a clamp which holds it on to a bed rail or stretcher rail. At the other end are two unipivotal hinges at right angles for supporting and rotating the limb in different positions. A gutter is provided to hold the limb in question. It is clear that although an arm is illustrated, the two hinges are not intended to track the elbow and this is not a device which can be readily viewed as adaptable to early post-arthroplasty use.

Apart from these devices, there exist shoulder abduction pillows which are tetrahedral pillows of foam, usually with a linen cover. Clearly an abduction pillow allows no progressive restriction and no range of motion, and is bulky. It is also limited even in respect of the fixed positions it can provide.

The present invention provides an orthopaedic brace for the upper limb which is particularly suitable for use following open or arthroscopic surgery of the shoulder by virtue of having no parts which contact the wound(s) or perioperative site.

According to the invention there is provided an orthopaedic brace for the upper limb comprising a mounting member adapted to be fastened to the torso of a patient, an arm support pivotally mounted on the mounting member for movement about vertical and horizontal axes, and an adjustment mechanism for raising and lowering the arm support about the horizontal axis to enable the shoulder joint of the patient to be abducted over a continuous range from a low abduction angle to a high abduction angle and abducted over a continuous range from a high abduction angle to a low abduction angle.

The device according to the invention suitably has a waistband hinged to an adjustable upright side bar which can be set for different patient heights without the need to make a series of sizes—this gives a marked saving on hospital or clinic inventory. Near its upper end the mounting member is suitably provided with a partial chest band and both this and the waist band have securing straps. The purpose of the hinge at the waistband is to allow the upright components to find their natural "lie" against the side of the patient and this feature is in marked contrast to prior art upper limb braces.

At the upper end of the relatively rigid mounting member is a mechanism for controlling motion of the shoulder joint. The mechanism includes a generally cylindrical pylon supported by the mounting member with the longitudinal axis of the pylon extending generally vertically. A connecting element is supported at the upper end of the pylon and is joined to an arm support in a manner that permits pivotal movement of that arm support about a generally horizontal pivot axis and also allows rotational movement of the connecting element and arm support about the pylon's vertical axis. Two carrier members—a first and a second carrier member—are supported by the pylon below the connecting element. The two carrier members are spaced vertically apart and are supported for pivotal movement about the vertical longitudinal axis of the pylon. The first carrier member is secured against longitudinal sliding movement relative to the pylon and the second carrier element is longitudinally slidable along the pylon. An elevator link has one end pivotally connected to the second carrier member and an opposite end pivotally connected to the arm support at a point intermediate the length of that support. Screw adjusting means extends between the first and second carrier members and is operable for selectively positioning the second carrier member at any of an infinite number of positions over a continuous range of adjustment along the length of the pylon. Operation of such means therefore adjusts and sets the angle of abduction of the arm support without preventing rotation of the arm support about the longitudinal vertical axis of the pylon.

The pylon may either be rotatably mounted or fixed in relation to the mounting member. If the pylon is rotatable, then the two carrier members are supported for rotation along with the pylon—that is, they are incapable of independent rotation in relation to the pylon. On the other hand, if the pylon is fixed in position (relative to the mounting member) then the two carrier members are supported for rotation about the supporting pylon.

In a preferred embodiment the pylon is fixed and has an arcuate, circumferentially-extending groove. One of the carrier members is provided with a radial opening alignable with that groove, and a motion-controlling element in the form of a pin is insertable through the opening of the carrier member and into the groove for limiting the extent of rotation of the carrier members, and of the arm support connected thereto, about the vertical axis of the pylon. Most advantageously, the pylon also includes an opening extending radially inwardly at one end, and preferably at each end, of the groove so that, if desired, the pin may be inserted through the opening of the carrier member and into an aligned radial opening at the end of the groove in the pylon to lock the arm support against rotation about the longitudinal axis of the pylon.

The arm support includes at least two sections, an upper arm support and a lower arm support, joined by an elbow hinge for pivotal movement of the two sections about a generally vertical pivot axis. The elbow hinge includes upper and lower hinge plates with opposing contact surfaces, one of the surfaces having an arcuate groove concentric with the vertical pivot axis and the other plate having an aperture registrable with that groove. Motion limiting means in the form of an insert element or pin is insertable into the aperture and groove for limiting the extent of relative angular movement of the two sections of the arm support. If desired, holes may also be formed at one or both ends of the groove so that the pin may be used to lock the sections against further pivotal movement when the pin reaches the ends of the groove.

The screw adjusting mechanism for controlling the abductive angle of the arm support takes the form of a screw shaft and an adjusting nut threaded thereon. The adjusting nut is held captive in a recess formed in one of the carrier members. Rotation of the nut causes the other carrier member to move vertically towards or away from the nutretaining carrier member with such movement changing the position of the elevator link and, hence, the angle of the arm support connected to that link.

Other features, objects, and advantages will become apparent from the specification and drawings.

DRAWINGS

DETAILED DESCRIPTION OF PREFERRED EMBODIMENT

Figure 1:
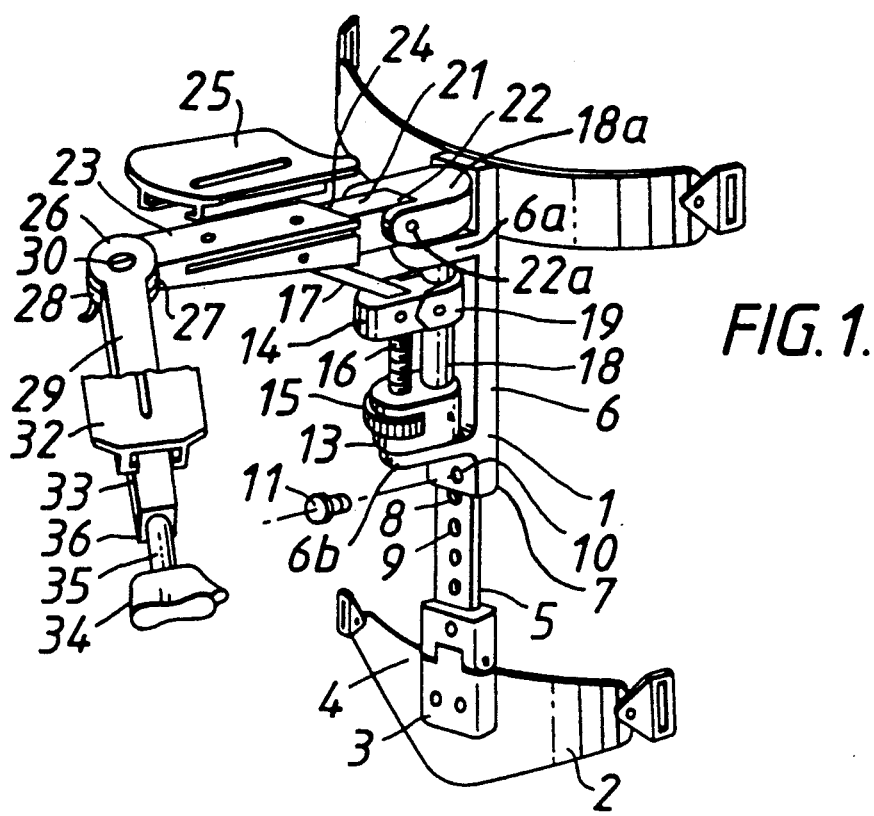
FIG. 1 is a general perspective view of an orthopaedic shoulder brace according to the invention with straps, liners, and harness omitted.

Referring first to FIG. 1, an orthopaedic brace 1 for an upper limb has a waistband 2 which is fitted centrally near its upper margin 4 with a yoke hinge 3. An upright bar 5, conveniently of stainless steel, is attached to yoke hinge 3, the axis of which is anterio-posterior when the device is fitted to a patient.

A mounting member 6, conveniently formed of rigid plastics material, has a longitudinal slot, the lower entry of which is indicated at 7, for receiving bar 5. The upright bar has multiple holes, two of which are indicated at 8 and 9. Mounting member 6 has a single hole 10 substantially of the same diameter as holes 8 and 9. A peg 11, which may be of metal or plastics, fits hole 10 and has a head 12 enlarged so that it may be conveniently grasped. The function of peg is described below with reference to FIG. 2.

The shoulder control mechanism is attached to mounting member 6. It includes a first carrier member 13 and a second carrier member 14. The first carrier member retains a captive nut 15 which drives an adjuster screw 16. The second carrier member is pivotally connected to one end of an elevator link 17, and both carrier members are supported by a cylindrical pylon 18 which has a vertically-disposed longitudinal axis. The lower first carrier member is secured against longitudinal sliding movement with respect to the pylon but the second carrier member, equipped with a collar 19 that extends about the pylon, is slidable upwardly and downwardly along that pylon. In the embodiment depicted in FIG. 1, the pylon is rotatably supported by upper and lower lateral extensions 6a and 6b of mounting member 6. The upper end of the pylon extends through upper extension 6a and carries a connecting element or member 18a. Being fixed to the pylon, the connecting element is rotatable with the pylon about its vertical axis.

The elevator link 17 has its opposite end pivotally connected to arm support 21 at a point intermediate the length of that support. As shown in FIG. 1, the proximal end 22 of the arm support is pivotally connected by pivot pin 22a to the connecting element 18a at the upper end of pylon 18. Since the arm support and connecting element are rotatable with the pylon about the pylon's vertical axis, the arm support 21 is pivotal about two axes—the vertical axis of the pylon and the horizontal axis of pivot pin 22a.

The arm support 21 has two sections hinged together for relative movement about a vertical axis. The upper or proximal arm support section 23 is extensible and includes a slidable member 24 on which an upper arm shell 25 is mounted. The proximal section 23 and slidable member 24 are non-circular in cross section, and although capable of telescopic sliding movement, are locked against relative rotation about their longitudinal coaxis. Such a construction prevents rotation of the humerus and shoulder joint which could lead to deleterious effects in the post-surgical shoulder, although other embodiments can be contemplated in which both limited and unlimited rotation might be accommodated. At the same time, the arrangement allows the upper arm section of the brace to be extended for longer upper arm lengths.

Elbow hinge 26 includes an upper plate 27 continuous with upper arm support 23 and a lower plate 28 continuous with lower or distal arm support section 29. The two hinge plates are joined together by screw 30. The elbow hinge plates 27 and 28 are adapted internally to provide a motion control system as described below with reference to FIG. 5.

The lower or distal arm support 29 carries a lower arm shell 32 in a bilateral slot 33. Hand support body 34 is moulded, conveniently in foamed plastics such as polyurethane, over frame member 35 which in turn is rotatably supported by slide 36 that forms a part of lower arm support 29. The hand support is fully profiled on both surfaces so that by rotating the frame 180 degrees it may be converted from left-handed to right-handed use. The frame and slide arrangement allows the distal section 29 of the arm support 21 to be extended for longer arm lengths and the slot mount for the distal shell 32 allows optimal positioning of and support for the lower arm. In addition, the frame allows the wrist and forearm considerable freedom to rotate. Embodiments are contemplated which do not allow wrist rotation and which provide limited ranges of motion in both handed and non-handed versions.

Figure 2:
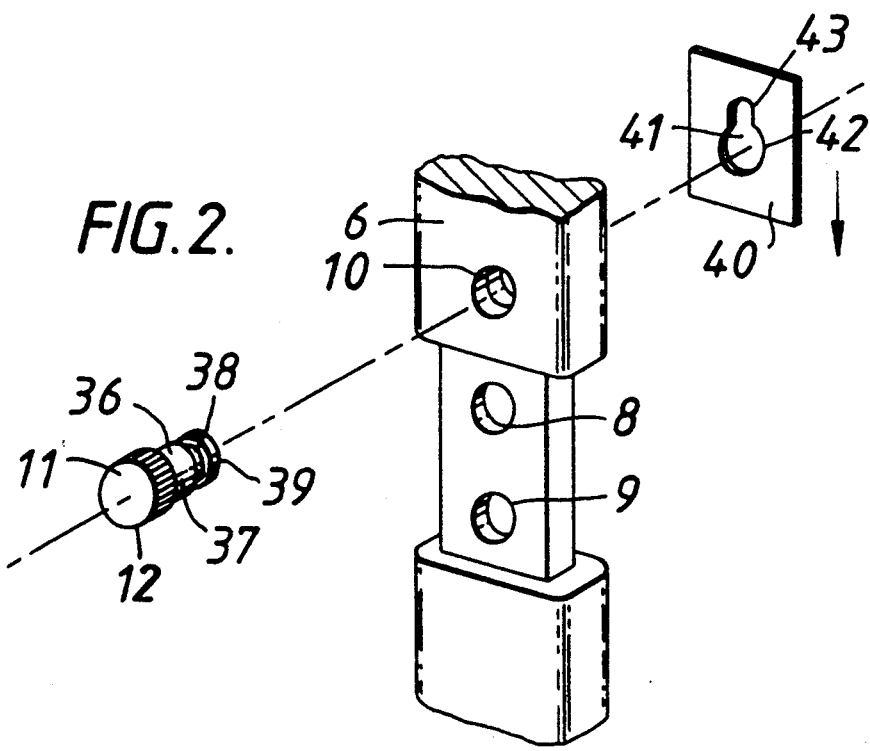
FIG. 2 is an exploded perspective view of the mechanism for adjusting the vertical dimension of the brace.

Turning now to FIG. 2, pin or peg 11 is shown aligned with hole 10. The shank 36 of the pin has a proximal portion 37, the diameter of which is the same as that of holes 8, 9, and 10. The proximal portion 37 extends along the shank for distance equal to the thickness of mounting member 6. The shank 36 has an intermediate portion 38, the diameter of which is less than that of holes 8, 9, and 10. Distal portion 39 of shank 36 has a diameter equal to that of proximal portion 37. A locking plate 40 has a hole 41 with a round portion 42 just larger than distal portion 39 and a slot portion 43 just larger than intermediate portion 38, respectively, of shank 36. With the pin or peg 11 withdrawn, upright bar member 5 is extended or pushed home to the position required, insuring that hole 11 in mounting member 6 is aligned with a hole such as 8 or 9. The peg 11 is then pushed into hole 10. Round portion 42 of hole 41 in the locking plate 40 is pushed over distal portion 39 of shank 36. The locking plate is then slid downwardly so that the slot portion 43 passes around intermediate portion 38 and under distal portion 39 of shank 36.

It is contemplated to provide an embodiment with a gravity lock wherein the intermediate portion 38 lies directly under a hole, say 8, in upright bar 5 and is slightly longer than the thickness of bar 5, as well as having a reduced diameter. When the device is in use, gravity determines that upright bar 5 will drop against the upper aspect of intermediate portion 38, effectively locking it between distal portion 39 and proximal portion 37. In a further contemplated embodiment, all three locking features are present and the locking plate is housed by locally thickening the rear portion of the mounting member 6 to form a recess.

Figure 3:
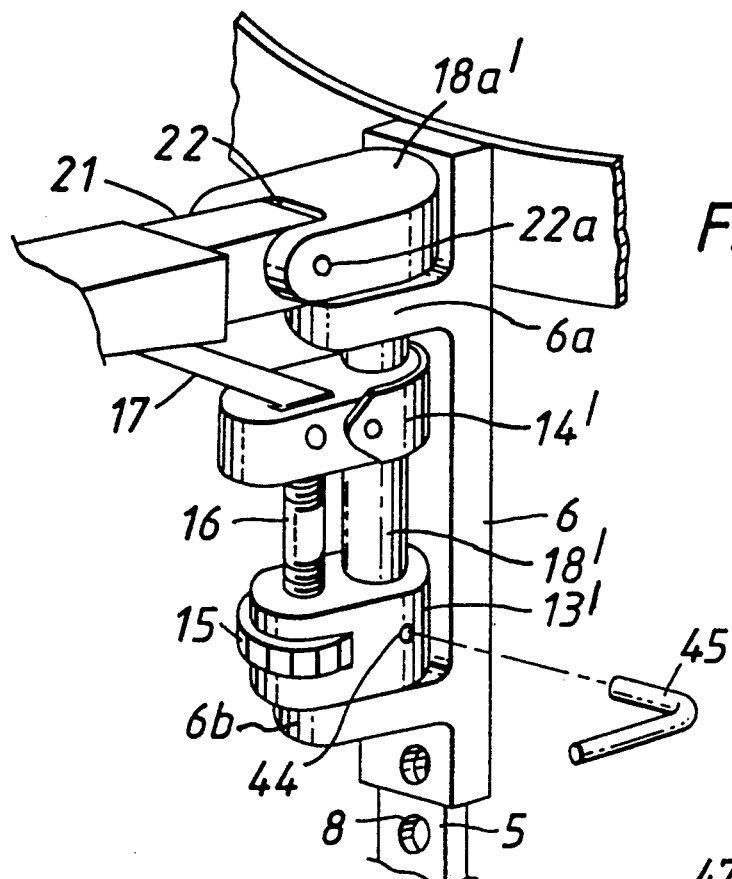
FIG. 3 shows a perspective view of a modified shoulder brace adjusting mechanism.

In the embodiment of FIG. 3, the shoulder adjusting mechanism has major components generally disposed as previously described with reference to FIG. 1. However, in the embodiment of FIG. 3, the cylindrical pylon 18' is fixed rather than rotatable with respect to mounting member 6 and the first and second carrier members 13' and 14', respectively, as well as connecting element 18a', are rotatably supported by the pylon. In addition, means are provided for limiting the extent of rotation of lower carrier member 13', upper carrier member 14', connecting element 18a', and arm support 21 about the longitudinal vertical axis of pylon 18'.

Figure 4A:
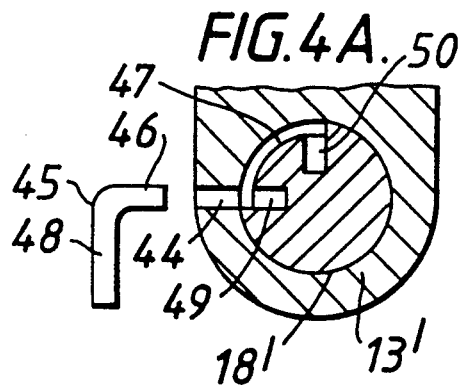
FIG. 4A is a horizontal cross sectional view taken along line 4A—4A of FIG. 4.
Figure 4:
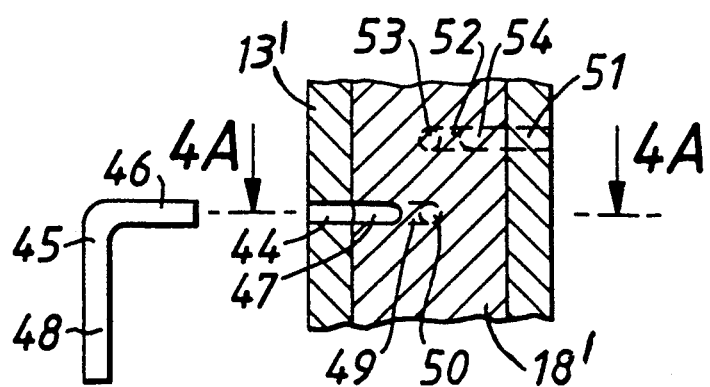
FIG. 4 is a vertical cross sectional view of part of the mechanism depicted in FIG. 3.

Referring to FIGS. 4 and 4A, that part of pylon 18' extending through the lower or first carrier member 13' is provided with an arcuate, circumferentially extending slot or groove 47. A radially-extending opening or hole 44 is located in the wall of the first carrier member 13' and is alignable with groove 47. A motion controlling element 45 of L-shaped configuration has a shorter arm 46 and a longer arm 48 and, when the shorter arm is inserted through the opening 44 of the carrier member and into groove 47 of the pylon, the extent of relative rotation will be limited to the angular extent of the groove which, in the embodiment shown, is 90 degrees. It will also be observed that the pylon includes radial openings 49 and 50 extending inwardly to a depth greater than groove 47 with such openings being dimensioned to receive the end of the longer arm 48 of element 45. Therefore, if the user wishes to lock the carrier members and arm support 21 against rotation about the vertical axis of the pylon, arm 48 may be inserted through openings 44 and 49, or through openings 44 and 50, to immobilise parts against such rotation.

The L-shaped motion control element or pin may also be used in conjunction with holes 51, 52 and 53 (the latter being shown in hidden detail in FIG. 4 and offset for clarity) and groove 54 to form a second set of lock stops and a second motion control system for use when the device is applied on the opposite shoulder.

Figure 5:
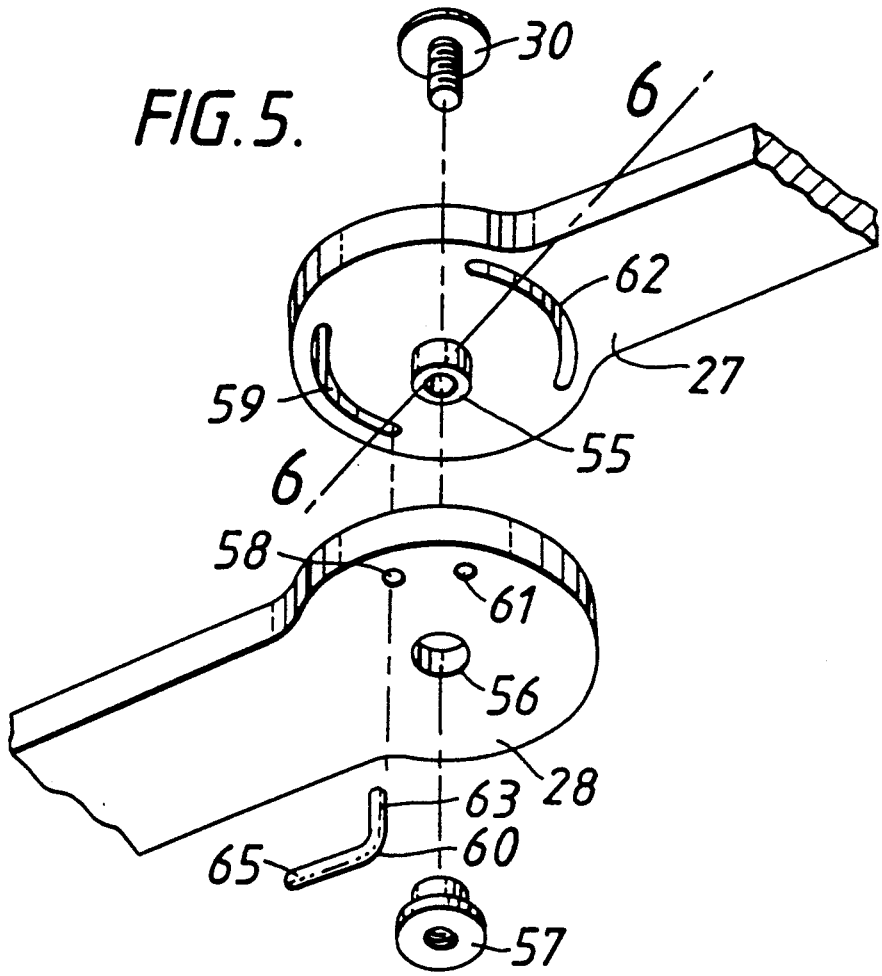
FIG. 5 is an exploded perspective view of the elbow hinge showing the adjustment mechanism.

In FIG. 5, the principal components of elbow hinge 26 are shown in exploded perspective view. Upper plate 27 has a boss 55 which is received in hole 56 in lower plate 28. The screw 30 is secured in place by nut 57. When the parts are in assembled condition, hole or opening 58 in lower plate 28 lies concentrically with groove 59 in upper plate 27. A motion-controlling element 60 may be used to limit the extent of pivotal movement about the vertical axis of the elbow hinge. When the shorter arm 63 of the L-shaped motion-controlling element or pin 60 is inserted into opening 58 of lower plate 28, it enters groove 59 of the upper plate, thus allowing the hinge a range of flexion limited by the angular extent of the groove (90 degrees in the embodiment illustrated). A second opening 61 is provided in the lower plate and lies concentrically with groove 62 in the upper plate and also cooperates with the motion-controlling element 60 to limit the range of flexion when the device is worn on the patient's opposite side.

Figure 6:
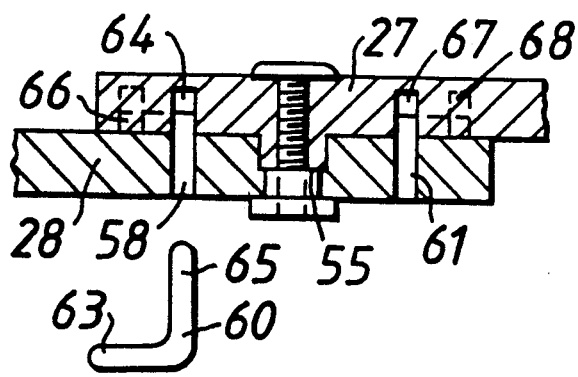
FIG. 6 is a sectional view taken along line 6—6 of FIG. 5, but showing the parts in assembled condition.

As indicated in FIG. 6, when the longer arm 65 of element 60 is inserted into opening 58 of lower plate 28, it may extend into the deeper hole or opening 64 of the upper plate, locking the two components against pivotal movement. If the lower plate is rotated 90 degrees, the longer arm of element 60 may be pushed into opening or hole 66 (shown in hidden detail) of upper plate 27, locking the two components in a second position of adjustment.

Similarly, in FIG. 6, it can be seen from the lines of hidden detail that when the longer arm 65 of element 60 is pushed into hole 61 of lower plate 28, it may penetrate into hole 67 of upper plate 27, thereby locking the two components together. If the lower plate 28 is rotated about boss 55 through 90 degrees, the longer arm 65 of element 60 may be pushed into hole 68 (shown in hidden detail) of upper plate 27, thereby locking the two components in a second position of adjustment. Thus, the hinge is provided with zero degrees and 90 degrees flexion stops for left or right arm use.

Figure 7:
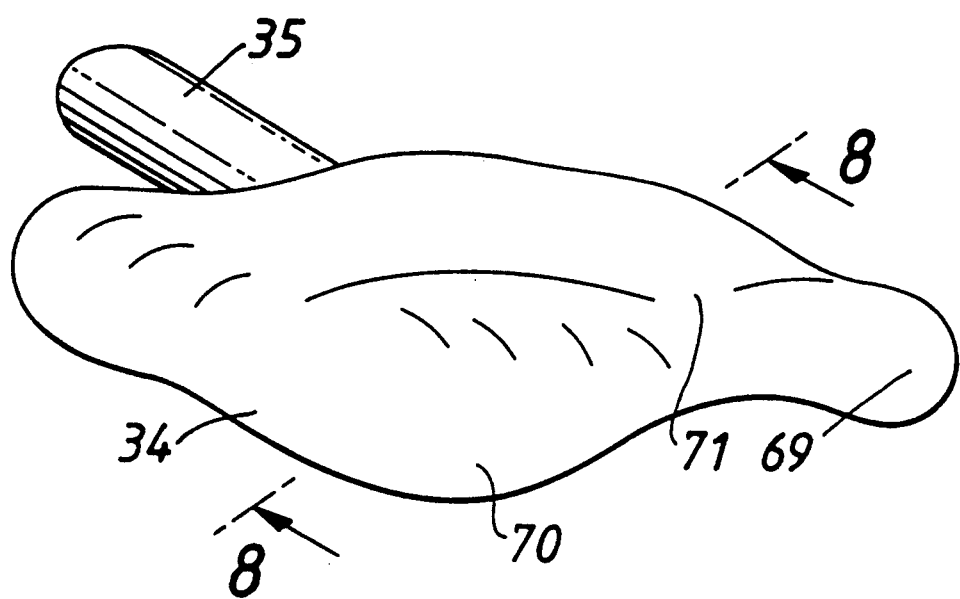
FIG. 7 is a perspective view of a hand support.

Turning now to FIG. 7, there is shown a hand rest component 34 which has a thumb rest 69, differentiated from the main portions 70 by a sulcus 71. This component is conveniently moulded in foamed plastics over frame 35.

Figure 8:
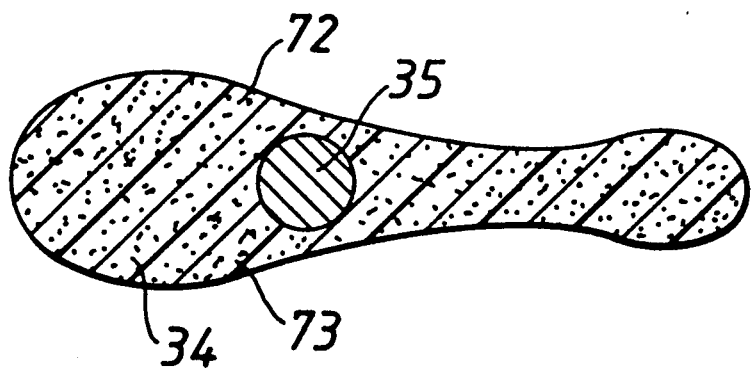
FIG. 8 is a sectional view of the hand support taken along line 8—8 of FIG. 7.

FIG. 8 is a cross sectional view of support 34 showing the identical upper and lower profiles 72 and 73, respectively. Rotation through 180 degrees about frame 35 allows left or right handed use.

Figure 9:
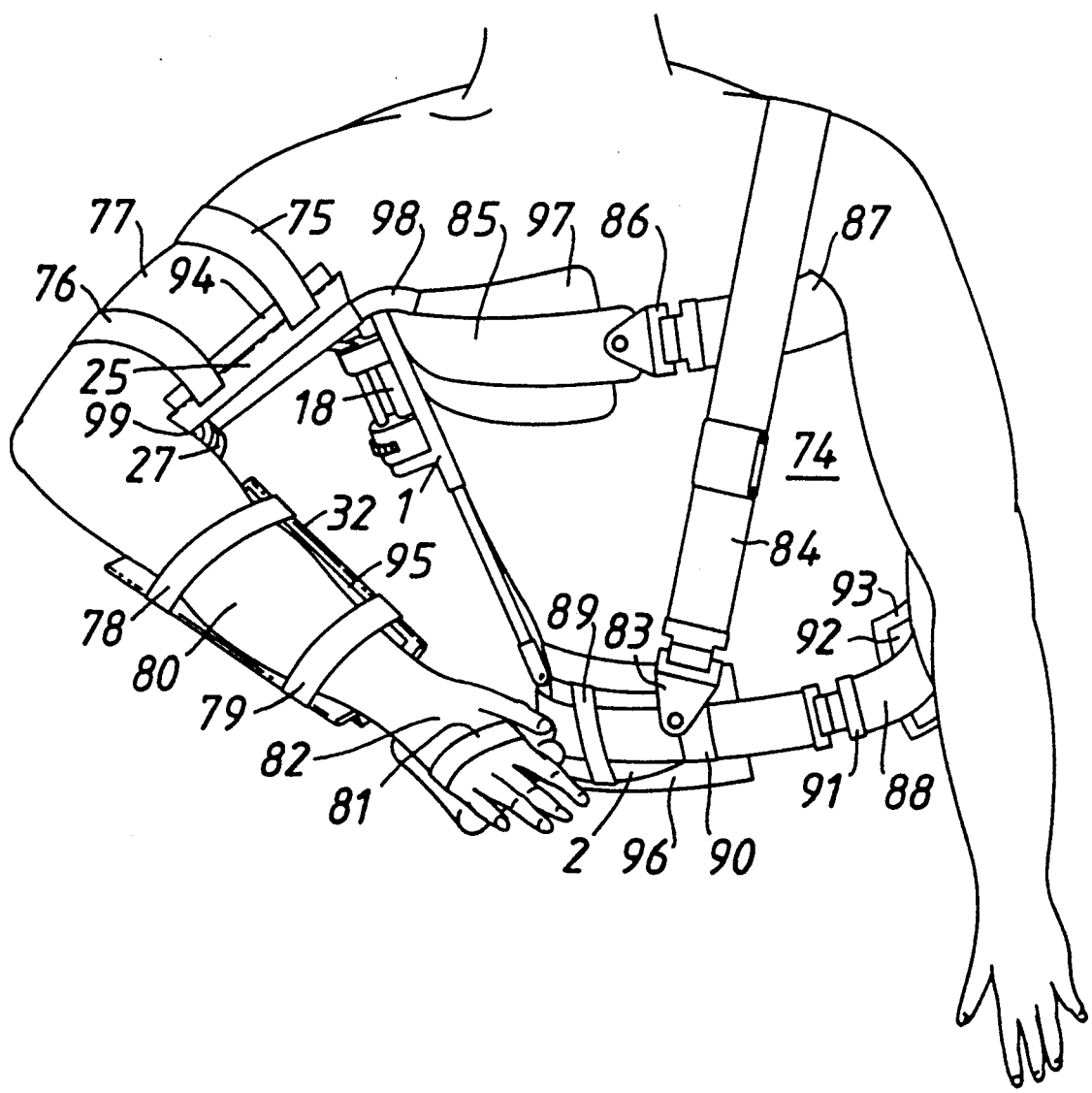
FIG. 9 is a perspective view showing the brace in position on a patient, including harness and straps.

FIG. 9 illustrates other features of the orthopaedic brace 1 for the upper limb in place on a patient 74. Straps 75 and 76 conveniently made of loop and pile material secure upper arm 77 on shell 25. Straps 78 and 79 are similar and secure lower arm 80 on lower arm shell 32. Strap 81 is also similar and secures hand 82 on hand support 34.

Waistband 2 is fitted with two identical quick release buckles, one near each end, only one of which can be seen at 83. Shoulder suspension belt 84 is attached between the quick release buckles and is adjustable. Chest band 85 has a quick release buckle at each end, only one of which can be seen at 86. Chest belt 87 is attached between the quick release buckles and is adjustable. Waist belt 88 is secured to waistband 2 with loops, two of which can be seen at 89 and 90. Waistband 88 is adjustable and secured to itself with a quick release buckle 91.

Waistband 88 is also provided with a contralateral pad 92 which has a soft liner 93. Shells 25 and 32 are provided with liners 94 and 95. Liners are provided for waistband 2 and chest band 85, indicated at 96 and 97, respectively. Moulded foam pads are provided for the top of pylon 18 and elbow hinge upper plate 27 at 98 and 99, respectively.

We claim:

1. An orthopaedic brace for the upper limb comprising a mounting member equipped with fastening means for attachment to a patient's torso; a cylindrical pylon having a generally vertical longitudinal axis supported by said mounting member; an arm support having proximal and distal ends; a connecting element pivotally connected to said proximal end of said arm support for pivotal movement of said arm support relative to said pylon about a generally horizontal axis extending transversely with respect to said arm support; said connecting element also being supported at the upper end of said pylon for pivotal movement of said connecting element and arm support about the pylon's vertical longitudinal axis; first and second carrier members supported by said pylon below said connecting element; said carrier members being spaced apart and supported for pivotal movement about said vertical longitudinal axis of said pylon; said first carrier member being secured against longitudinal sliding movement relative to said pylon and said second carrier element being longitudinally slidable along said pylon; an elevator link extending between and connecting said second carrier member and said arm support; and screw adjusting means extending between and connecting said first and second carrier members for selctively positioning said second carrier member at any of an infinite number of positions lengthwise of said pylon for adjusting and setting the angle of abduction of said arm support without obstructing rotation of said arm support about said longitudinal vertical axis of said pylon.

2. The brace of claim 1 in which said pylon is supported by said mounting member for rotation about said longitudinal vertical axis; said carrier members and said pylon being fixed against relative rotation about said longitudinal vertical axis.

3. The brace of claim 1 in which said pylon is fixed to said mounting member and said carrier members are rotatably supported by said pylon.

4. An orthopaedic brace for the upper limb comprising a mounting member equipped with fastening means for attachment to a patient's torso; a cylindrical pylon having a generally vertical longitudinal axis supported by said mounting member; an arm support having proximal and distal ends; a connecting element pivotally connected to said proximal end of said arm support for relative pivotal movement of said arm support about a generally horizontal axis; said connecting element also being supported at the upper end of said pylon for pivotal movement of said connecting element and arm support about the pylon's vertical longitudinal axis; first and second carrier members supported by said pylon below said connecting element; said carrier members being spaced apart and supported for pivotal movement about said vertical longitudinal axis of said pylon; said first carrier member being secured against longitudinal sliding movement relative to said pylon and said second carrier element being longitudinally slidable along said pylon; an elevator link extending between and connecting said second carrier member and said arm support; and screw adjusting means extending between and connecting said first and second carrier members for selectively positioning said second carrier member at any of an infinite number of positions lengthwise of said pylon for adjusting and setting the angle of abduction of said arm support without obstructing rotation of said arm support about said longitudinal vertical axis of said pylon; said pylon being tied to said mounting member and said carrier members being rotatably supported by said pylon; said pylon having an arcuate circumferentially-extending groove and one of said carrier members having a radial opening alignable with said groove; and a motion-controlling element insertable through said opening into said groove for limiting rotation of said arm support about said vertical axis to the angular extent of said groove.

5. The brace of claim 4 in which said pylon includes at least one radial opening extending inwardly beyond said groove; said radial openings of said pylon and said one of said carrier members being alignable for receiving said motion-controlling element to lock said arm support against relative rotation about said vertical axis.

6. The brace of claim 1 in which said elevator link is pivotally connected at opposite ends to said arm support and to said second carrier member, respectively.

7. The brace of claim 1 in which said second carrier member is disposed above said first carrier member.

8. The brace of claim 7 in which screw adjusting means comprises a threaded shaft and an adjusting nut threaded thereon; said first carrier member having a bore slidably receiving said screw shaft and having a recess in which said nut is captured; and said second carrier member having a socket rotatably receiving the upper end portion of said screw shaft.

9. An orthopaedic brace for the upper limb comprising a mounting member equipped with fastening means for attachment to a patient's torso; a cylindrical pylon having a generally vertical longitudinal axis supported by said mounting member; an arm support having proximal and distal ends; a connecting element pivotally connected to said proximal end of said arm support for relative pivotal movement of said arm support about a generally horizontal axis; said connecting element also being supported at the upper end of said pylon for pivotal movement of said connecting element and arm support about the pylon's vertical longitudinal axis; first and second carrier members supported by said pylon below said connecting element; said carrier members being spaced apart and supported for pivotal movement about said vertical longitudinal axis of said pylon; said first carrier member being secured against longitudinal sliding movement relative to said pylon and said second carrier element being longitudinally slidable along said pylon; an elevator link extending between and connecting said second carrier member and said arm support; and screw adjusting means extending between and connecting said first and second carrier members for selectively positioning said second carrier member at any of an infinite number of positions lengthwise of said pylon for adjusting and setting the angle of abduction of said arm support without obstructing rotation of said arm support about said longitudinal vertical axis of said pylon; said arm support comprising an upper arm support section and a lower arm support section joined by elbow hinge means for relative pivotal movement of said sections about a generally vertical pivot axis; said elbow hinge means comprising upper and lower hinge plates having opposing contacting surfaces; one of said surfaces having an arcuate groove concentric with said vertical pivot axis and the other of said plates having an aperture registrable with said groove; and motion-limiting means insertable into said aperture and said groove for limiting the extent of relative angular movement of said upper and lower sections.

10. The brace of claim 9 in which said groove-providing hinge plate has an opening at least at one end of said groove deeper than said groove; said opening being dimensioned to receive said motion-limiting means when said motion-limiting means is fully inserted through said aperture for locking said arm support sections against pivotal movement about the vertical axis of said elbow hinge means.

* * * * *